United States Patent
Hamilton, II et al.

(10) Patent No.: US 8,274,649 B2
(45) Date of Patent: Sep. 25, 2012

(54) FAILURE DETECTION IN LIGHTING SYSTEMS

(75) Inventors: Rick A. Hamilton, II, Charlottesville, VA (US); Paul A. Moskowitz, Yorktown Heights, NY (US); Brian M. O'Connell, Cary, NC (US); Clifford A. Pickover, Yorktown Heights, NY (US); Keith R. Walker, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 18 days.

(21) Appl. No.: 12/399,825

(22) Filed: Mar. 6, 2009

(65) Prior Publication Data

US 2009/0316147 A1 Dec. 24, 2009

Related U.S. Application Data

(63) Continuation-in-part of application No. 12/145,406, filed on Jun. 24, 2008, now Pat. No. 7,518,715.

(51) Int. Cl.
*G01J 1/42* (2006.01)

(52) U.S. Cl. ........ 356/218; 356/226; 356/229; 340/638; 315/291

(58) Field of Classification Search .......... 356/121–123, 356/213–235; 250/226; 340/636, 638, 664; 315/219; 705/6
See application file for complete search history.

(56) References Cited

U.S. PATENT DOCUMENTS

| | | | |
|---|---|---|---|
| 4,220,412 A * | 9/1980 | Shroyer et al. ........ 356/218 |
| 4,508,996 A | 4/1985 | Clegg et al. | |
| 4,827,119 A * | 5/1989 | Gaboury ........ 250/214 R |
| 5,037,798 A | 8/1991 | Etzbach et al. | |
| 5,061,997 A | 10/1991 | Rea et al. | |
| 5,099,313 A | 3/1992 | Suemoto et al. | |
| 5,307,058 A | 4/1994 | Tokizane et al. | |
| 5,548,398 A | 8/1996 | Gaboury | |
| 6,515,275 B1 * | 2/2003 | Hubel et al. ........ 250/226 |
| 6,542,082 B1 | 4/2003 | Nowka et al. | |
| 6,784,667 B2 * | 8/2004 | Belenger et al. ........ 324/414 |
| 7,114,830 B2 | 10/2006 | Robertson | |
| 7,206,072 B2 | 4/2007 | Takahashi et al. | |
| 7,249,865 B2 | 7/2007 | Robertson | |
| 7,262,690 B2 | 8/2007 | Heaton et al. | |
| 7,355,523 B2 | 4/2008 | Sid | |
| 7,382,454 B1 * | 6/2008 | Turner ........ 356/416 |
| 7,518,715 B1 | 4/2009 | Hamilton, II et al. | |

(Continued)

FOREIGN PATENT DOCUMENTS

GB 2405734 * 4/2003

(Continued)

OTHER PUBLICATIONS

"Microcontrollers Provide Power Control for Lighting Applications", Steve Bowling, ECNasiamag.com, 4 pages, Apr. 1, 2008.

(Continued)

*Primary Examiner* — Hoa Pham
(74) *Attorney, Agent, or Firm* — Mark C. Vallone; The Salehi Law Group (57) ABSTRACT

A method and apparatus for continuous monitoring of a light bulb or group of light bulbs. The light emission of a light bulb is compared with known emission failure values for similar types of light bulbs, and a determination of a near failure status for the bulb is made.

20 Claims, 7 Drawing Sheets

U.S. PATENT DOCUMENTS

| | | | |
|---|---|---|---|
| 2004/0201448 | A1 | 10/2004 | Wang |
| 2004/0225384 | A1* | 11/2004 | Onishi et al. ............ 700/90 |
| 2005/0086100 | A1 | 4/2005 | Yanagisawa et al. |
| 2005/0225263 | A1 | 10/2005 | Van Egmond |
| 2006/0049935 | A1 | 3/2006 | Giannopoulos et al. |
| 2006/0249663 | A1* | 11/2006 | Ewig et al. ............ 250/221 |
| 2008/0019113 | A1 | 1/2008 | Smith |
| 2008/0105620 | A1 | 5/2008 | Hicks |
| 2008/0218171 | A1 | 9/2008 | Keith et al. |
| 2008/0246950 | A1* | 10/2008 | Ono ............ 356/51 |
| 2009/0159779 | A1* | 6/2009 | Lu ............ 250/205 |

FOREIGN PATENT DOCUMENTS

| | | |
|---|---|---|
| JP | 2006339740 | 12/2006 |
| WO | WO 96/36202 | 11/1996 |

OTHER PUBLICATIONS

Bernstein et al., Climate Change 2007: Synthesis Report, Summary for Policymaker, http://www.ipcc.ch/pdf/assessment-report/ar4/syr/ar4_syr_spm.pdf.

Veitch, J.A. et al.; "Modulation of Fluorescent Light: Flicker Rate and Light Source Effects on Visual Performance and Visual Comfort", Lighting Research and Technology, v. 27, No. 4, 1995, pp. 243-256, http://irc.nrc-cnrc.gc.ca/pubs/fulltext/nrcc38944/nrcc38944.pdf.

http://ioannis.virtualcomposer2000.com/spectroscope/toyspectroscope.html (retrieved Apr. 30, 2012).

http://ioannis.virtualcomposer2000.com/spectroscope/amici.html#diagram (retrieved Apr. 30, 2012).

* cited by examiner

FAILURE DETECTION IN LIGHTING SYSTEMS

1. CROSS REFERENCE TO RELATED APPLICATION

This application is a continuation-in-part of application entitled "Method for Determination of Efficient Lighting Use" filed on Jun. 24, 2008 and bearing application Ser. No. 12/145,406, the disclosure of which is incorporated herein in entirety for background information.

2. FIELD OF THE INVENTION

The invention relates generally to remote detection of a source of light and more specifically to the determination of bulb type and intensity of light emitted from the bulb from a distance.

3. DESCRIPTION OF THE RELATED ART

The IPCC, Intergovernmental Panel on Climate Change, has stated in their summary report of 2007 that most of the temperature increases seen by the world are most likely caused by anthropogenic GHG, greenhouse gas, emissions. Climate change resulting from greenhouse gas emissions has resulted in international agreements on limiting and reducing such emissions, for example, the Kyoto agreement. Even in the United States, a country that has not ratified the Kyoto agreement, there is movement to reduce greenhouse gas emissions by reducing the use of energy. The US Energy Independence and Security Act of 2007 mandates an energy efficiency increase of 30 percent for light bulbs by 2012. In effect, this will result in the replacement of incandescent light bulbs (ILBs), by compact fluorescent lights (CFLs), or light emitting diodes (LEDs) by 2012. Compact fluorescent lights and LEDs are more efficient sources of light because they convert more of the electricity used into light and less into wasted heat.

The desirability of and the law in the US for reducing electric energy use will require the replacement of traditional ILBs by CFLs or LEDs. It difficult or impossible to tell the difference through remote visual inspection between the types of bulbs if the bulb structure is hidden. The bulb may be contained within a frosted envelope or not viewed directly. The appearance of the light emitted is very similar for most CFLs and ILBs. The direction of the CFL industry is to produce bulbs which have a color appearance similar to that of ILBs. It is desirable to determine the bulb type quickly and easily from a distance to aid in the replacement of ILBs by CFLs in large installations. It is also desirable to determine the compliance with the law by households, businesses, and governments.

SUMMARY

Although the total appearance of the emitted light may look similar, the intensity of light from light bulbs of different types differs in the time domain. Traditional ILBs emit light through the mechanism of radiation from a heated filament. The light intensity is constant in the time domain. Fluorescent bulbs (including CFLs), and LEDs emit light that is characterized by rapid variations of intensity in time.

The invention provides a method for discriminating based upon the time-varying characteristics of the light sources to determine which type of bulb is in use. In an alternative aspect, the emission spectrum of the light sources is used to discriminate between CFLs and LEDs, and ILBs. CLFs and LEDs show a spectrum of distinct emission lines, while ILBs show a continuous spectrum of light.

The present invention permits the remote inspection of light sources, which is advantageous when lights are not easily accessible for close visual inspection. A user may desire to remotely inspect light sources during migration from ILBs to CFLs and LEDs to determine which bulbs have already been replaced. Additionally, companies and governments may desire to use the present invention to ensure compliance.

In one aspect, the present invention provides a method including receiving light from a plurality of light sources using an apparatus configured to analyze and detect a frequency of variation of light intensity; determining a type of light bulb and light intensity from the plurality of light sources based upon the detected frequency of variation of the light intensity, the frequency of variation being one of a multiple of a power company supply frequency and 20 to 60 kHz; determining the geographic area of the plurality of light sources; calculating the ratio of light intensities from efficient and inefficient lighting sources for the plurality of light sources within the geographic area and automatically reporting the ratio to one of a carbon offset provider and an enforcement agency; and reporting the determinations and calculation to a user.

BRIEF DESCRIPTION OF THE DRAWINGS

The foregoing features and other features of the present invention will be described with reference to the drawings. In the drawings, the same components have the same reference numerals. The illustrated embodiment is intended to illustrate, but not to limit the invention. The drawings include the following Figures.

DETAILED DESCRIPTION

The electricity supplied by power companies reverses polarity typically 110 or 120 times per second (supply of 60 Hz in US and 50 Hz in Europe), fluorescent lights turn on and off at that rate, which may cause a change in intensity or flicker. Incandescent lights do not produce this flicker because the light is produced by a hot glowing wire. This wire is not affected by electrical polarity switches, since the wire stays hot and glows steadily. Fluorescent-type lights and LEDs with high-efficiency ballasts may have a flicker rate of 20 kHz to 60 kHz.

Figure 1:
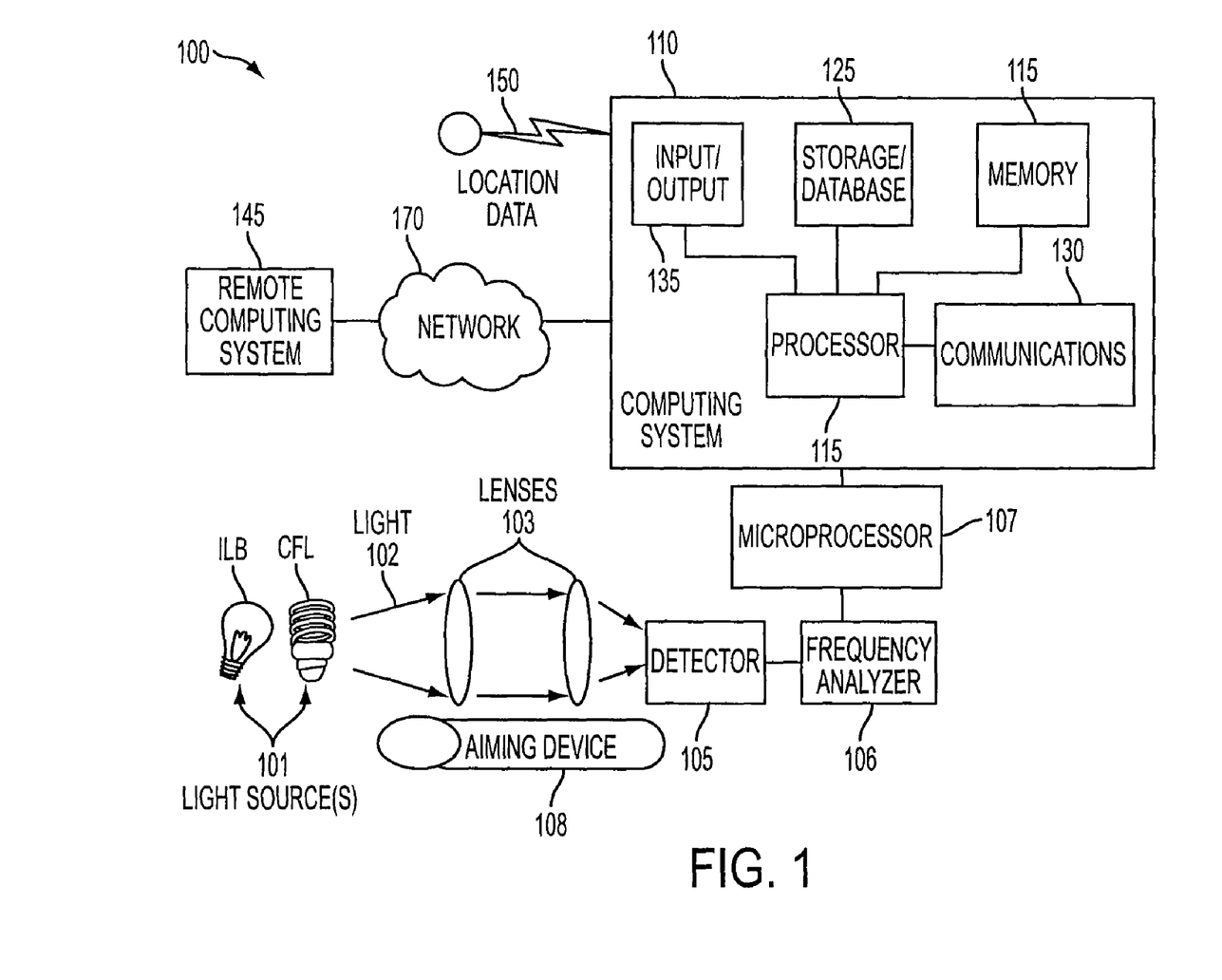
FIG. 1 is a schematic diagram of a system for determining a type of light source using time domain resolution in accordance with an embodiment of the present invention.

FIG. 1 is a schematic illustration of a system 100 for determining a type of light source from a plurality of light sources 101 using time domain resolution in accordance with an embodiment of the present invention. System 100 uses these innate characteristics of differing light sources 101 to remotely ascertain the type of light source.

As shown in FIG. 1, lens or lenses 103 on a detector 105 may be used to focus light 102. Detector 105 may include or be built into a small hand-held portable or mobile device, which may be equipped with wireless communication capabilities such as Wi-Fi (IEEE 802.11a, b, or g), mobile phone, or Bluetooth. Additionally, to aid in the aiming of detector 105, it may be fitted with an optical aiming device 108 including, for example, lenses, or a laser pointer. Laser pointers may employ a helium-neon laser for example. Such lasers are now built into small battery-powered "pocket pointers" for use in lectures.

An analyzer 106, which may include time domain or frequency dependant electronic filters may be used to distinguish among an ILB with a relatively constant level of light intensity, and that of fluorescent bulbs or LEDs that have a 120 Hz, or 20 kHz or above time variation in light intensity. An example of a time domain or frequency analyzer is the RSA3000B Series of Real-Time Spectrum Analyzers manufactured by the Tektronix Corporation. The use of a light source 101 other than an ILB may be determined by measuring the frequency of change of the light intensity.

The results of the frequency analysis may be transferred to a microprocessor 107 including logic to discern bulb types based on measurements gathered from analyzer 106. Microprocessor 107 may also calculate the ratio of the maximum light intensity to the minimum light intensity for one cycle. For an ILB, the ratio may be approximately one; for other light sources there may be a much greater ratio of maximum to minimum intensity.

The output of microprocessor 107 may be reported to a simple display (not shown) or a computing system 110 that may perform further analysis. Computing system 110 may include a processor and memory 115, a storage/database 125, a communications module 130 and an input/output capability 135.

Additionally, system 100 may receive input from a geographic positioning system, for example, a GPS satellite or a wireless phone system, to incorporate position or location data 150 that may be transferred over a network 170 to computing system 110. For instance, computing system 110 may detect and record the location of ILB street lamps that need to be exchanged for CFLs.

In one embodiment, the analysis for a group of light sources 101, or integrated light sources may be sent through network 170 to a remote computing system 145 acting in a monitoring function associated with, for example, an enforcement agency. The detection integration may be for an individual, company, or town. The integrated light may be analyzed for relative intensities of efficient and inefficient sources and a ratio may be calculated. For instance, the ratio of efficient lighting use to inefficient lighting use may be determined for a geographical area including a building, a block of buildings or a larger geographic area or political area, such as a town, county, state, or country. Observations of the larger areas may be conducted from tall buildings, towers, aircraft or satellites.

For example, if an overall analysis of a street or town indicates less than a threshold use of CFLs (for example, less than 20% of the bulbs), then a signal may be transmitted to a carbon-offset provider. Such a provider normally takes an action (for example, plants trees) to offset carbon use or to offset or mitigate deleterious actions. Services may be used to manage such signals. Profiles stored in databases may specify and control the amount of offset. Similarly, an automatic signal may be sent to a service that issues a fine, a warning, or takes another action against an individual, group, government, and the like. CFL bulbs may be sent to users as a result of such an analysis. Similarly, such signals may trigger rewards (for example, congratulation letters, rebates, decrease in payments, bonuses, coupons, discounts) to individuals or groups.

Figure 2:
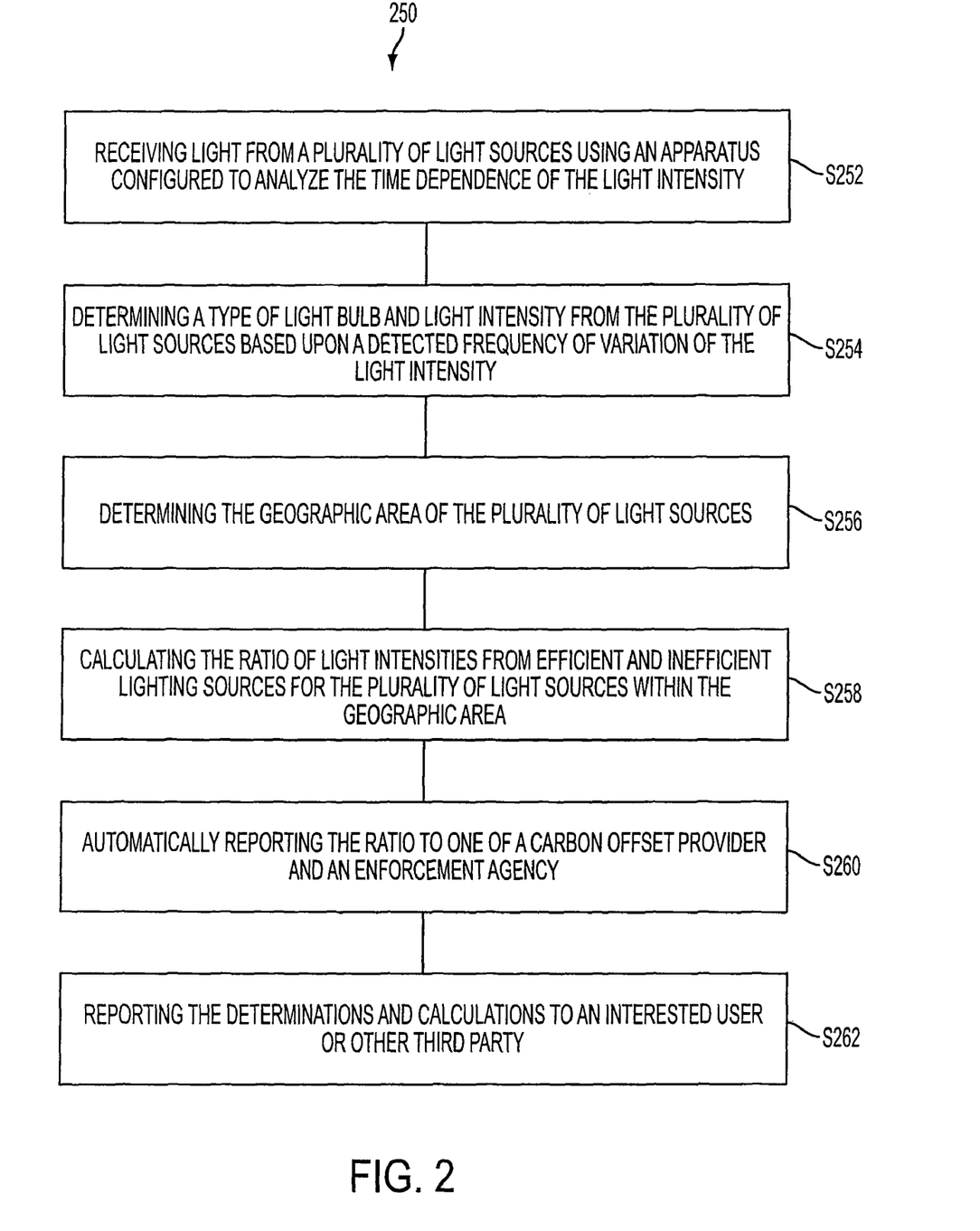
FIG. 2 is a flow diagram of a method for determining a type of light source using time domain resolution in accordance with an embodiment of the present invention.

FIG. 2 is a flow diagram of a method 250 for determining a type of light source using time domain resolution in accordance with an embodiment of the present invention. In one embodiment, method 250 includes receiving light from a plurality of light sources using an apparatus configured to analyze the time dependence of the light intensity (s252); determining a type of light bulb and light intensity from the plurality of light sources based upon a detected frequency of variation of the light intensity (s254). The frequency of variation being one of a multiple of a power company supply frequency and 20 to 60 kHz.

Method 250 also includes determining the geographic area of the plurality of light sources (s256); calculating the ratio of light intensities from efficient and inefficient lighting sources for the plurality of light sources within the geographic area (s258) and automatically reporting the ratio to one of a carbon offset provider and an enforcement agency (s260). Once method 250 has been completed or as desired the determinations and calculation are reported to the interested user or other third party (s262).

Figure 3:
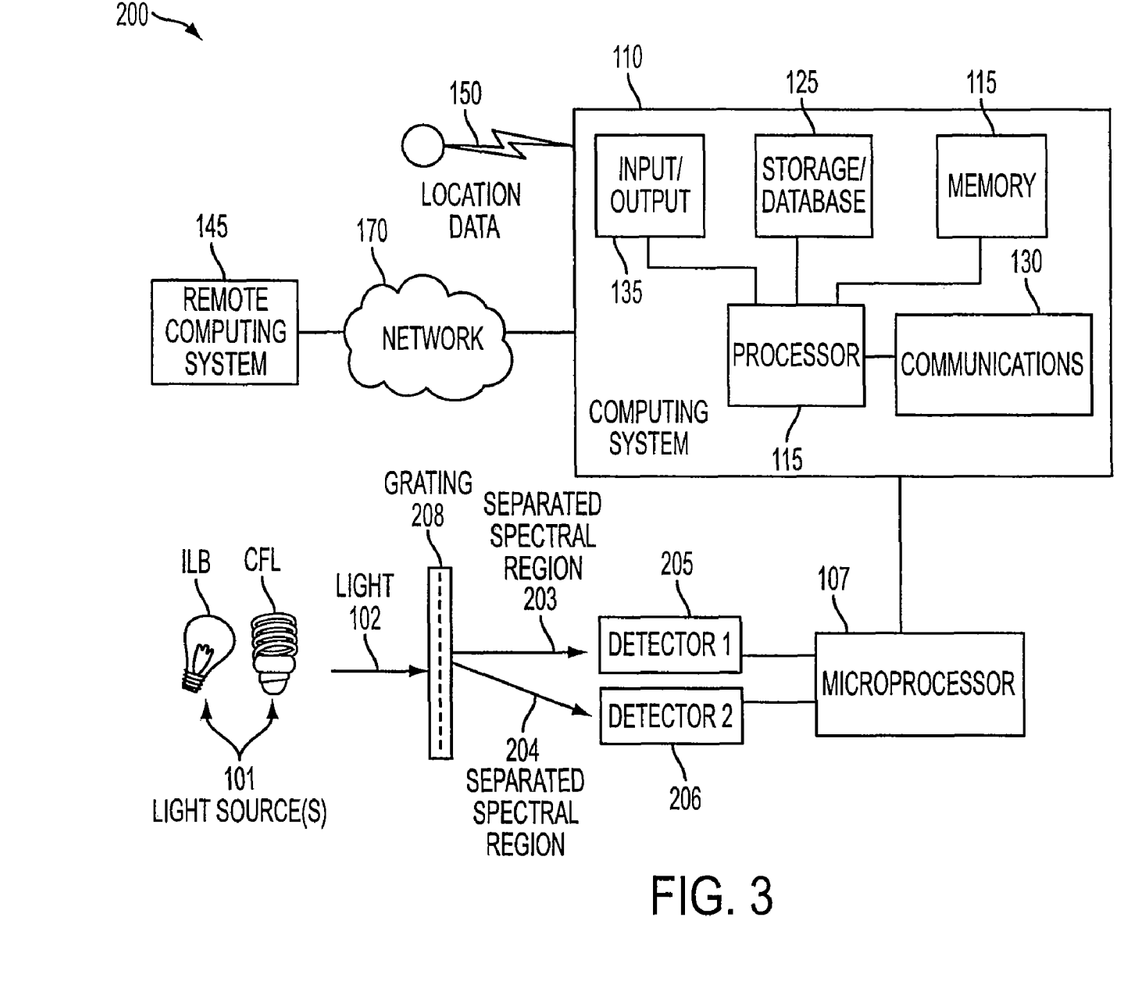
FIG. 3 is a schematic diagram of a system for determining a type of light source using the emission spectrum of the light source in accordance with an embodiment of the present invention.

FIG. 3 is a schematic diagram of a system 200 for determining a type of light source 101 using the emission spectrum of light source 101 in accordance with an embodiment of the present invention. In this embodiment, the emission spectrum is used as a means of discrimination between CFLs and ILBs.

Fluorescent lights including CFLs normally use a small amount of mercury vapor in their discharge. Atomic mercury produces both visible and ultraviolet UV light in its emission spectrum. The visible light adds to the total illumination directly. The UV light excites phosphors in the inner wall of the lamp envelope to produce light of the desired color.

Because CFLs use mercury, they display strong atomic mercury emission lines at 436 nm (blue), 546 nm (green), and a pair at 577 nm and 579 nm (yellow-orange), as well as UV lines at 254 nm and 184 nm. A large fraction of the emitted light is in these lines, with much lower emission in the space between the lines. The 436, 546 and 577-579 nm lines are especially bright. The light appears to be like that of an ILB. However the ILB spectrum is continuous.

LEDs (light-emitting diodes) are generally monochromatic, each LED having one color wavelength. Illumination lamps made of LEDs may use three different color LEDs to produce a white light. When analyzed, the spectrum of an LED lamp will have distinct lines, usually one each of red, green, and blue. The analysis used below for CFLs may also be applied to LED lamps.

In the visible spectrum of CFL, the strong 546 nm green mercury line is in the center. The yellow mercury 577-579 group is to the left of center and the blue mercury 436 nm line is to the right of center. There is a deep valley in intensity between the green and yellow lines, also between the green and blue lines.

In the visible spectrum of ILB, the intensity changes slowly over the visible spectrum and is approximately unchanged over adjacent segments.

In one embodiment, referring to FIG. 3, light 102 from a light source 101, such as a bulb, either ILB or CFL, passes through a grating 208 where it is separated into its spectral components 203 and 204, according to the well known grating formula:

$$d \sin q = nl \quad \text{(EQ. 1)}$$

In Equation 1, d is the Grating Spacing, q is the Angle of Refraction, n is the order of the spectrum and l is the wavelength of the light. Longer wavelengths (i.e. red) are refracted at greater angles than are shorter wavelengths (i.e. blue). Accordingly, specific regions of the spectrum may be directed to separate detectors, such as detectors 205 and 206. Their intensities in terms of voltage or current in detectors 205 and 206 are then directed to a microprocessor 107 where the intensities are compared and a determination is made whether the light is from an ILB or CFL.

For example, comparing the intensity of a region cantered on the 546 nm line compared to that of a region centered on the gap between 546 and 577 nm, at around 560 nm, the ratio of brightness for a CFL may be at least 10:1, while for a ILB it may be about 1:1.

The output of microprocessor 107 may be reported to the simple display (not shown) or computing system 110 for further use and analysis as stated above.

The apparatus may employ mirrors and lenses for directing and focusing the light. Instead of a grating, a prism may be employed or glass filters may be used.

Figure 4:
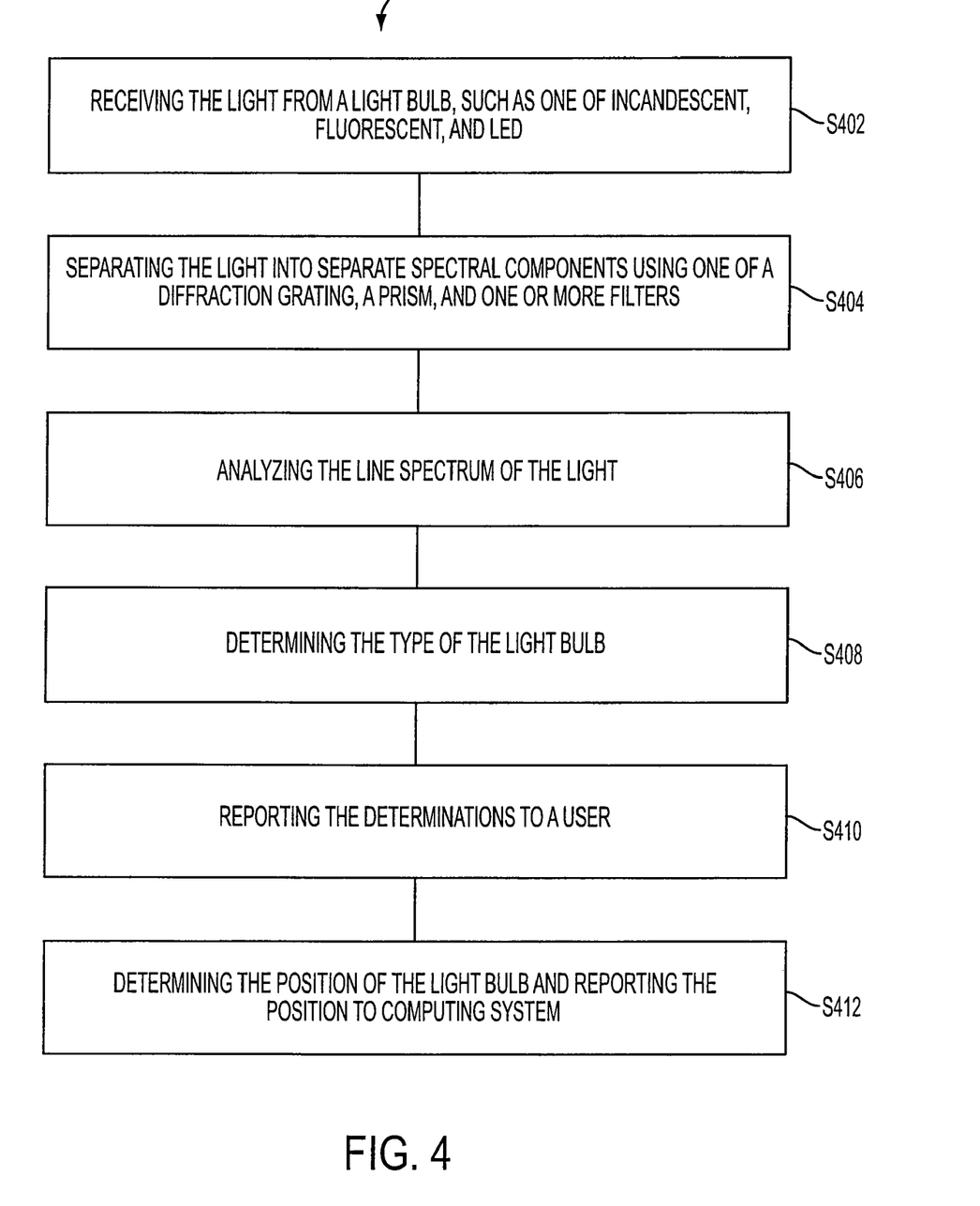
FIG. 4 is a flow diagram of a method for determining a type of light source using the emission spectrum of the light source in accordance with an embodiment of the present invention.

FIG. 4 is a flow diagram of a method 400 for determining a type of light source using the emission spectrum of the light source in accordance with an embodiment of the present invention 1. In one embodiment, method 400 includes receiving a light emission from a light bulb, such as one of incandescent, fluorescent, and LED (s402), separating the light into a spectrum of light having separate spectral components using one of a diffraction grating, a prism, and one or more filters (s404), analyzing the line spectrum of the light (s406), determining the type of the light bulb (s408) and reporting the determinations (s410) to a user.

On one embodiment, the determination is made by determining the ratio of intensities of the gap between spectral lines with the intensity of the spectral line. The lines may include one or more of the mercury 546 nm line, the mercury 436 nm line, and the mercury 577-579 nm lines.

In yet another embodiment, method 400 may include determining the position of the light bulb and reporting the position to computing system 110 (s412).

In another embodiment, the present disclosure can be used for failure prediction of lighting systems. Light sources undergo changes in their emissions prior to failure. These changes are reflected in the intensity and emission characteristics of the light source. The apparatus of FIG. 1 and the apparatus of FIG. 3 can be used to detect the changes and to predict light source failure before the failure occurs.

In the case of incandescent fluorescent light sources, including compact fluorescent (CFL) and LED sources, light intensity diminishes before failure. For incandescent bulbs, the filament, typically tungsten, can evaporate during the lifetime of the bulb. The evaporated tungsten can coat the inner surface of the bulb and block light emission.

In the case of fluorescent bulbs, the vaporized mercury in the bulbs may be slowly driven into the phosphor that coats the inner surface of the bulb, and also into the glass of the bulb which also includes phosphor. Thus, light output is reduced as the mercury is exhausted from the discharge. In the case of LED bulbs, many different failure modes may cause the light output to be reduced, such as, for example, phosphor degeneration, metal diffusion, and thermal stress.

Additionally, impending failure of the light sources can result in changes in the color spectrum of the light sources. For incandescent bulbs, the filament burns hotter as material is evaporated. This results in a shift of the spectrum toward the blue spectra. In the case of fluorescent bulbs, as mercury is driven out of the discharge, the bright blue and green emission lines of the mercury fade and the lamp tends to take on a pinkish color supplied by the background glow of argon in the bulb. The argon is used to initiate the discharge. In this case, there is a shift towards the red spectra. In the case of LED bulbs which use a blue LED and have a phosphor coating inside the bulb, degradation of the phosphor can cause a shift of the light towards the blue spectra.

In an embodiment, the detector 105 shown in FIG. 1, or the detectors 205 and 206 shown in FIG. 2, can be used to monitor light intensity. The detector 105 provides a signal to the microprocessor 107, which is coupled to the computing system 110. Additionally, detectors 205 and 206 may be used to compare intensities of different spectral regions. Previous readings stored in the memory 115 may be compared by the processor 115 with current readings from the detector 105. Based on this comparison, a failure prediction can be made. Changes in the total intensity or shifts of spectral content for each type of bulb may be compared with the histories of each bulb which has failed in order to predict failure for active light sources.

Figure 5:
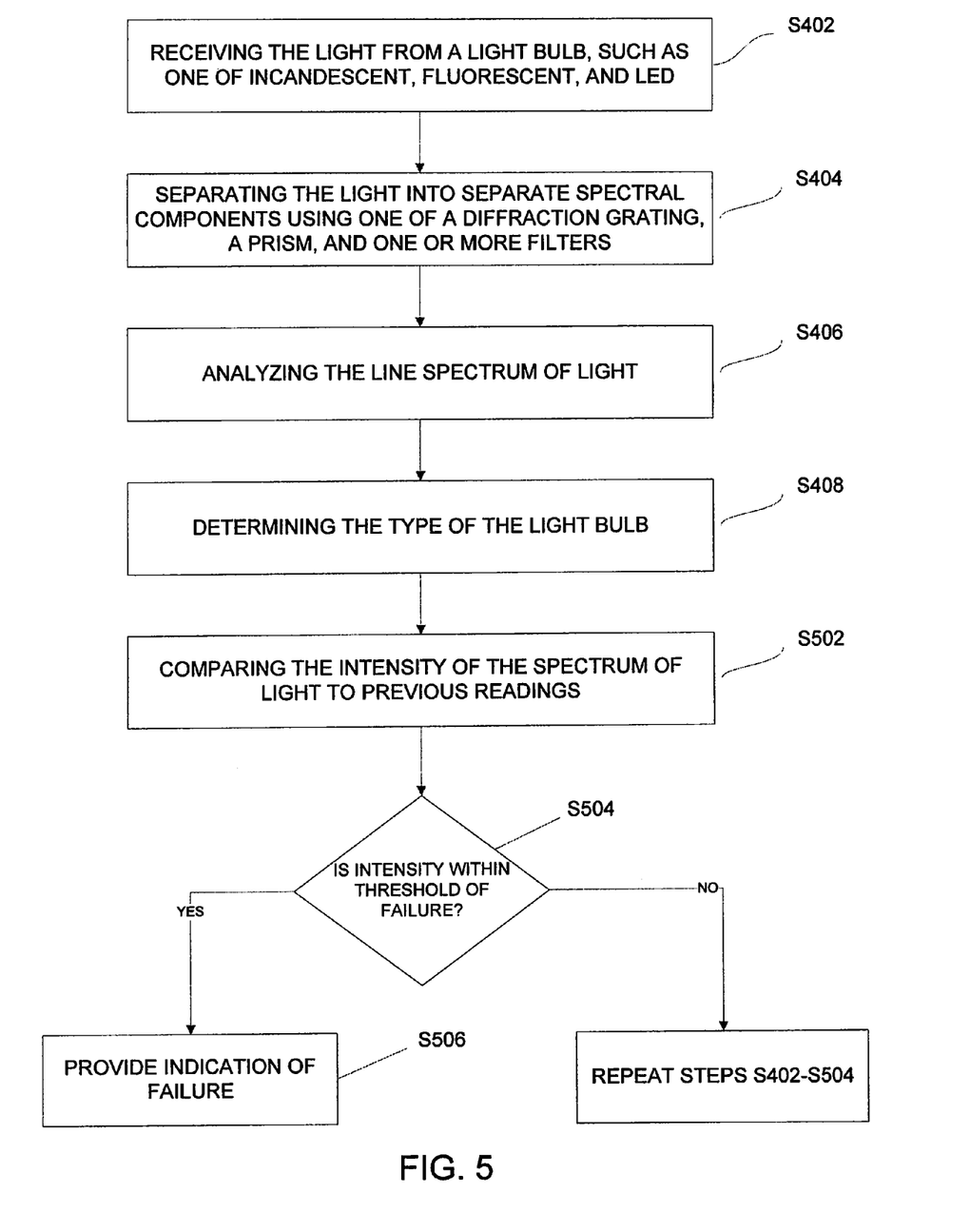
FIG. 5 is a flow diagram of a method for predicting a light source failure.

FIG. 5 is a flow diagram of a method for predicting a light source failure. The steps s402-s408 are the same as described above for FIG. 4. However, s406 includes the step of analyzing and determining the intensity of the light spectrum. The intensity can be measured as radiant intensity, radiant energy, radiant flux, radiant exitance/emittance, radiosity, spectral radiance, spectral irradiance, radiance, irradiance, luminous intensity, luminous energy, luminous flux, luminance, illuminance, luminous emittance, luminous efficacy, or brightness.

After the intensity of the light spectrum is determined, the intensity is compared to previous readings of failed bulbs of the same type. For example, if the bulb type is determined to be a fluorescent bulb at s408, then the intensity of the light spectrum is compared to failed fluorescent bulb readings at s504. These readings can be stored within the memory of the measuring device, or alternatively, stored in a memory at a remote location, such as a server, a base station or a central facilities management system.

The comparison of the intensity of the bulb can be made against known failure intensities provided by a bulb manufacturer, stored readings of failure intensities, an intensity failure value for a previously failed bulb in the same or different environment, or an average of intensity failure values for previously failed bulbs in the same or different environment.

If the intensity is within a certain percentage of known failure intensities for fluorescent bulbs, then an indication of possible failure is made at s506. In another embodiment, if the intensity is within a certain percentage or value that is close to known failure intensities, then an indication of possible failure is made at s506. The threshold for failure can be predetermined by the manufacturer, or pre-set by the user. For example, the user may specify that the intensity be within 2% of an average of failed intensities in order for an indication of failure to be provided. Table 1 below is an example of various intensity readings and settings which can indicate a failure.

TABLE 1

| Measured Bulb Intensity | Threshold for Failure | Failure Indication Provided? |
|---|---|---|
| 200 Lumens | <=50 Lumens | NO |
| 55 Lumens | Within 20% of 50 Lumens | YES |
| 50 Lumens | <50 Lumens | NO |

If at s504, the intensity does not meet a failure threshold, steps s402 through s504 are repeated. Thus, the present disclosure provides for continuous monitoring of a bulb or group of bulbs in, for example, an office building, airport, collection of streetlamps and lampposts, apartment complex, shopping mall, sports complex, or any area which requires periods of constant and continual lighting.

In another embodiment, the comparison can be made against previously stored readings of the same bulb. This embodiment is preferred in a scenario where a bulb has slightly different characteristics than other similar types of bulbs. The prior readings can be stored on the bulb's memory, or alternatively, at a remote location that is in communication with the bulb.

In an embodiment, the continuous monitoring can be conducted via a portable hand-held device as described above. The hand-held device can receive and analyze the light spectrum, and can compare the light intensity with known intensity failure values. The hand-held device can then provide an indication of failure or near failure. In another embodiment, the hand-held device receives the light spectrum, and transmits this spectral data to a remote processor, such as a central processing unit, where the light intensity is compared to known failure intensities. Once the light spectrum is analyzed by the remote processor, the determination of failure is transmitted back to the hand-held device, where an indication of failure is provided to the user. In an embodiment, the hand-held device is equipped with a communication means such as Wi-Fi (IEEE 802.11a, b, or g), mobile phone, or Bluetooth to communicate with the remote processor.

In another embodiment, a group of bulbs can be tested to determine if the group is at failure. The intensity of each individual bulb in a group is taken, and added together. If the collective intensity of the group of bulbs is within a threshold of a failure intensity for the group of bulbs, then a failure indication can be provided for the entire group of bulbs, instead of just an individual bulb. This embodiment may be useful for scenarios where the failure of a single bulb in a large group does not necessarily greatly diminish the luminance of the group of bulbs.

In another embodiment, the shift in spectral content of the bulb may be used to predict failure. In one embodiment, spectral content can be measured by the color of the light spectrum. The color of the light spectrum of the bulb can be compared against the color of the light spectrum just prior to failure of failed bulbs. For example, for incandescent bulbs, if the color of the light spectrum is light blue, this may indicate an upcoming failure, as failed incandescent bulbs have a blue light spectrum just prior to failure. However, for fluorescent bulbs, a pink light spectrum may indicate an upcoming failure, as failed fluorescent bulbs have a red light spectrum just prior to failure.

Figure 6:
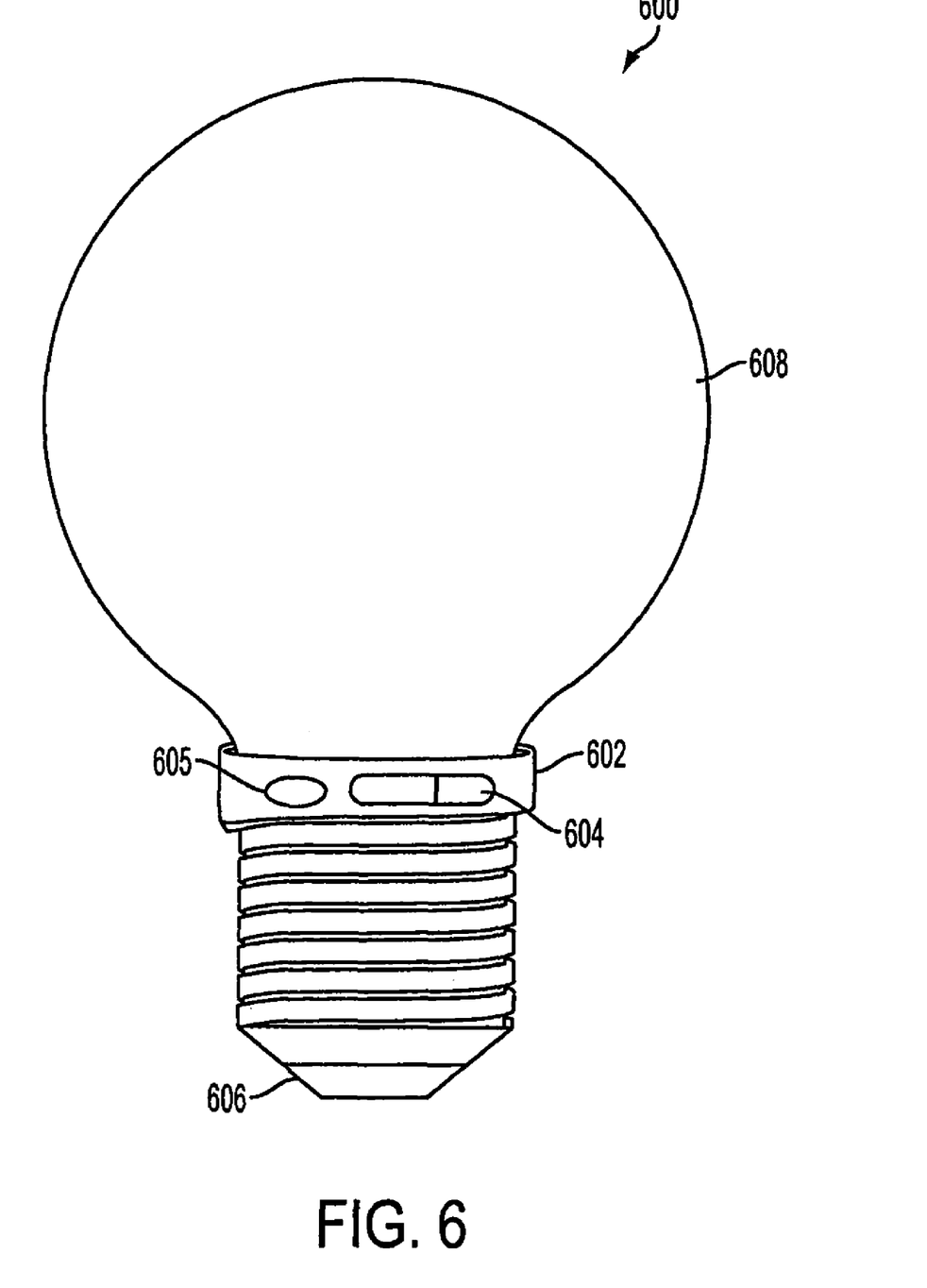
FIG. 6 is a view of a light bulb with a built-in apparatus for predicting a light source failure.

FIG. 6 is a view of a light bulb with a built-in apparatus for predicting a light source failure. In this embodiment, the apparatus to predict light failure is built into the actual light bulb. The light bulb 600 includes a socket 606 and a lamp bulb 608. A failure prediction circuit 602 is attached to the socket 606. The failure prediction circuit 602 is preferably mounted within a housing. An optical sensor 604 and at least one LED indicator 605 is attached adjacent to, on top of, or near the housing. The failure prediction circuit 602 can be attached in any manner to the socket 606 or the lamp bulb 608, and is not limited to the embodiment shown in FIG. 6.

The failure prediction circuit 602 also includes circuitry, such as a memory and a processor. The memory can store prior bulb light emission information, and the processor can be used to make failure calculations, such as the calculation shown in s504.

In an embodiment, the optical sensor 604 detects the amount of emitted light from the lamp bulb 608. Detecting the amount of emitted light means measuring the intensity of photons received from an emission source. The measured light is processed by the failure prediction circuit 602 as described in s502-s506 in FIG. 5. If the light is within a threshold of failure as determined in s502, then the LED indicator 605 is activated. The LED indicator 605 provides an indication that the bulb is at or nearing failure.

In an embodiment, the LED indicator 605 is colored green to indicate a healthy bulb. When the bulb is at or nearing failure, the LED indicator 605 is colored red. In another embodiment, the failure prediction circuit 602 includes multiple LED indicators. For example, one green LED that is active when the bulb is healthy, and one red LED that is active when the bulb is at or near failure. In yet another embodiment, the LED indicator 605 can flash to provide an indication.

In an embodiment, the failure prediction circuit 602 is powered by electricity conducted from the socket 606. Alternatively, the failure prediction circuit 602 can have an independent power source (not shown), such as a battery or a solar cell.

In another embodiment, the failure prediction circuit 602 can include an audible indicator, such as a speaker. The audible indicator is activated when the bulb is at or near failure, and can emit a monotone signal, a series of monotone signals, a chirping sound, a recorded voice alert, a musical tone, or any other type of audible indication.

In yet another embodiment, the failure prediction circuit 602 can be programmed to block electricity or electric flow to the light bulb 600 if the bulb is near failure. In another embodiment, the failure prediction circuit 602 can be programmed to blink the light bulb 600 if the bulb is near failure. Turning off the bulb by blocking electricity to it, or making the bulb blink both provide an indication that the bulb requires maintenance or replacement.

Figure 7:
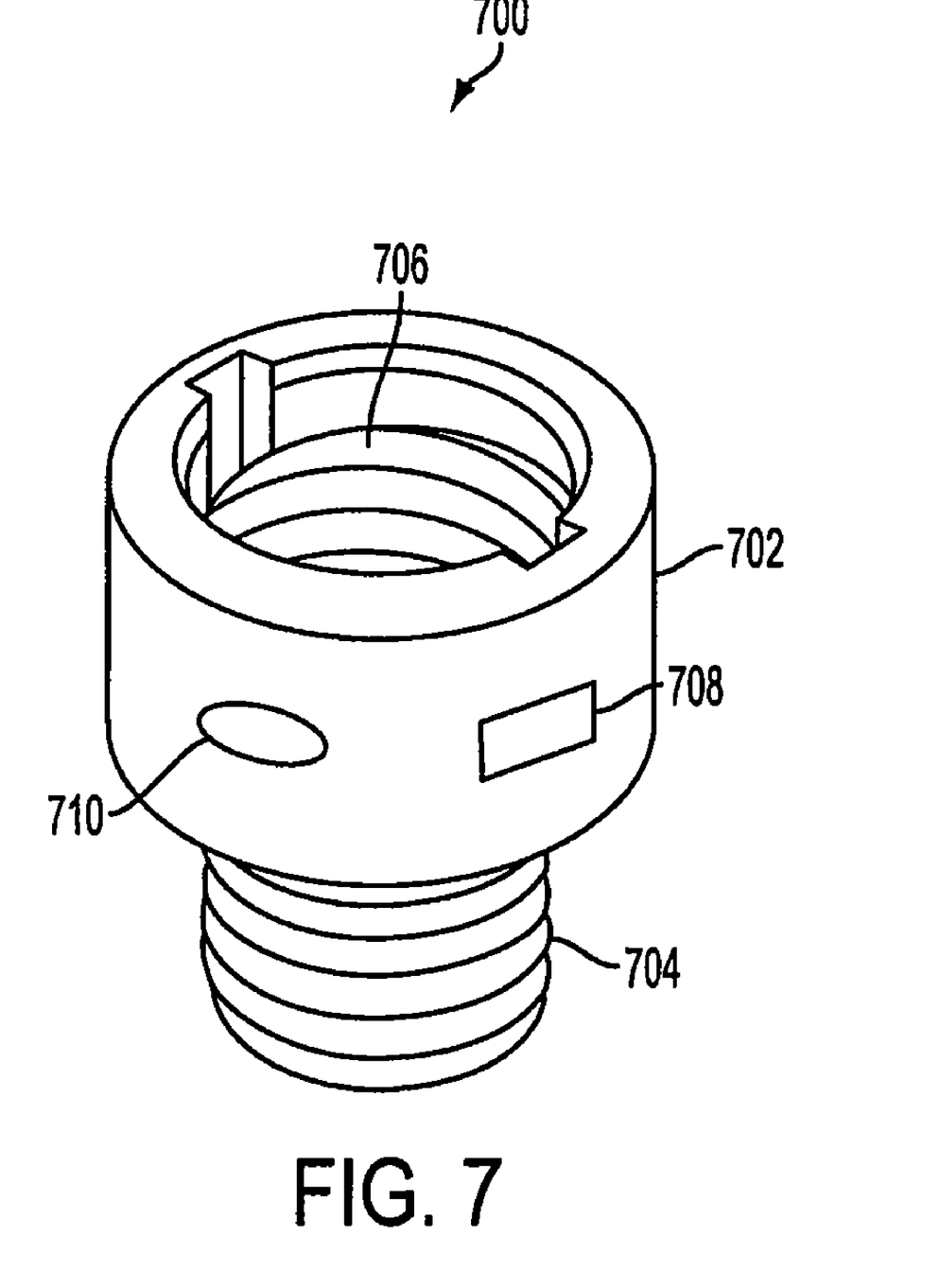
FIG. 7 is a view of a light socket with a build-in apparatus for predicting a light source failure.

FIG. 7 is a view of a light socket with a built-in apparatus for predicting a light source failure. In this embodiment, the apparatus to predict light failure is built into a light socket 700. The socket 700 includes a base 704 and housing 702. The socket 700 has an opening 706 which receives a base or a socket of a light bulb. In an embodiment, a failure prediction circuit similar to the one described in FIG. 6 is built into the housing 702.

The failure prediction circuit is encased within the housing 702 to protect the circuit from the environment, dust, wind, or other contaminants which might interfere with the operation of the circuit. The housing 702 includes an optical sensor 708 and an LED indicator 710. As described above, multiple types of indicators and actions (blocking electricity to the bulb, blinking the bulb, etc.) may be utilized to indicate a near failure condition.

In another embodiment, a rack having multiple light sockets similar to light socket 700 can be used to predict failure of a group of bulbs. The rack can have multiple light sockets and multiple optical sensors. However, the indicator would provide a near failure indication for the set of bulbs. For example, if the rack holds ten light bulbs, an indication is provided when at least half of the bulbs are near or at failure. The indication threshold can be pre-set or determined by the user, and the indication threshold can be a specific number of bulbs or a percentage value of the total number of bulbs.

In another embodiment, the light socket may be equipped with wireless communication capabilities such as Wi-Fi (IEEE 802.11a, b, or g), mobile phone, or Bluetooth. The wireless communication capabilities allows the light socket to receive and/or transmit data, such as bulb status, failure threshold values, and operational commands from a remote location, such as a server, a base station or a central facilities management system.

The invention has been disclosed in an illustrative manner. Accordingly, the terminology employed throughout should be read in an exemplary rather than a limiting manner. Although minor modifications of the invention will occur to those of ordinary skill in the art, it shall be understood that what is intended to be circumscribed within the scope of the patent warranted hereon are all such embodiments that reasonably fall within the scope of the advancement to the art hereby contributed, and that scope shall not be restricted, except in light of the appended claims and their equivalents.

What is claimed is:

1. A method for predicting a light source failure, comprising:
    receiving a light emission from a light source;
    separating the light emission into a light spectrum having separate spectral components;
    determining an intensity of the light spectrum;
    determining a light bulb type of the light source;
    comparing the intensity of the light spectrum with an intensity value of a failed light source having the same bulb type as the light source; and
    providing an indication of failure when the intensity of the light spectrum is within a threshold value of the intensity value of the failed light source.

2. The method of claim 1, wherein the light emission is received from one of a group consisting of an incandescent bulb, a fluorescent bulb, and light-emitting diode.

3. The method of claim 1, wherein the light emission is separated using one of a group consisting of a diffraction grating, a prism, and a filter.

4. The method of claim 1, wherein the intensity of the light spectrum is compared with a known failure intensity provided by a bulb manufacturer.

5. The method of claim 1, wherein the intensity of the light spectrum is compared with a stored intensity value of a previously failed light bulb.

6. The method of claim 1, wherein the intensity of the light spectrum is compared with an average intensity value of a plurality of previously failed light bulbs.

7. The method of claim 1, wherein the light emission is received at a hand-held device.

8. The method of claim 1, wherein the indication of failure is provided on a hand-held device.

9. An apparatus for predicting a light source failure, comprising:
    a light socket;
    a failure detection circuit electrically coupled to the light socket, the failure detection circuit having a sensor and at least one failure indicator;
    a memory storing a plurality of intensity failure values for a plurality of light bulb types; and
    a processor for comparing a light intensity value measured by the sensor with an intensity failure value, the processor further activating the at least one failure indicator.

10. The apparatus of claim 9, wherein the sensor is an optical sensor.

11. The apparatus of claim 9, wherein the at least one failure indicator is an audible indicator.

12. The apparatus of claim 9, wherein the at least one failure indicator is a visible indicator.

13. The apparatus of claim 9, further comprising a wireless communication means for receiving or transmitting data from a remote location.

14. The apparatus of claim 9, wherein the processor is further configured to block electrical flow from the light socket to a light bulb.

15. The apparatus of claim 9, wherein the failure detection circuit is encased within a housing.

16. The apparatus of claim 9, wherein the failure detection circuit is powered by one of a group consisting of a battery and a solar cell.

17. A self-failure predicting light bulb, comprising:
    a base;
    a lamp bulb electrically coupled to the base;
    a housing electrically coupled to the base;
    an optical sensor placed adjacent to the housing and configured to measure an intensity of light from the lamp bulb;
    a failure indicator placed adjacent to the housing for providing an indication of failure; and
    a failure detection circuit placed within the housing, the failure detection circuit having a processor and a memory,
    the memory configured to store an intensity failure value,
    the processor for comparing a light intensity value measured by the sensor with an intensity failure value, the processor further activating the at least one failure indicator.

18. The self-failure predicting light bulb of claim 17, wherein the processor is configured to blink the lamp when the light intensity value is within a threshold value of the intensity failure value.

19. The self-failure predicting light bulb of claim 18, wherein the threshold value is a percentage of the intensity failure value.

20. The self-failure predicting light bulb of claim 17, wherein the at least one failure indicator is configured to emit an audible indication selected from a group consisting of a monotone signal, a chirping sound, a recorded voice alert, and a musical tone.

* * * * *